(12) United States Patent
Liu

(10) Patent No.: US 10,722,606 B2
(45) Date of Patent: Jul. 28, 2020

(54) METHOD AND DEVICE FOR PRODUCING NEGATIVE OXYGEN IONS, AND METHOD AND DEVICE FOR PURIFYING AIR

(71) Applicant: Xiaoyue Liu, Shanghai (CN)

(72) Inventor: Xiaoyue Liu, Shanghai (CN)

(*) Notice: Subject to any disclaimer, the term of this patent is extended or adjusted under 35 U.S.C. 154(b) by 305 days.

(21) Appl. No.: 15/304,435

(22) PCT Filed: Apr. 15, 2015

(86) PCT No.: PCT/CN2015/076595
§ 371 (c)(1),
(2) Date: Oct. 14, 2016

(87) PCT Pub. No.: WO2015/158254
PCT Pub. Date: Oct. 22, 2015

(65) Prior Publication Data
US 2017/0028097 A1 Feb. 2, 2017

(30) Foreign Application Priority Data
Apr. 17, 2014 (CN) .......................... 2014 1 0155480

(51) Int. Cl.
*A61L 9/22* (2006.01)
*F24F 3/16* (2006.01)
(Continued)

(52) U.S. Cl.
CPC .................. *A61L 9/22* (2013.01); *A61L 9/145* (2013.01); *B01D 49/00* (2013.01); *B01D 53/00* (2013.01);
(Continued)

(58) Field of Classification Search
CPC .......... A61L 9/22; A61L 9/145; B01D 53/76; B01D 53/72; B01D 53/00; B01D 49/00; C02F 1/00; F24F 3/14; F24F 3/16
See application file for complete search history.

(56) References Cited

U.S. PATENT DOCUMENTS 5,728,288 A * 3/1998 Kubo .................. A61L 9/16
204/248
8,398,917 B2 * 3/2013 Itzhak .................. A61L 9/00
422/123
(Continued)

FOREIGN PATENT DOCUMENTS

CN 2257363 Y 7/1997
CN 203183866 U 9/2013
(Continued)

OTHER PUBLICATIONS

English translation of CN2257363 (Year: 1997).*
(Continued)

*Primary Examiner* — Regina M Yoo
(74) *Attorney, Agent, or Firm* — Quarles & Brady LLP

(57) ABSTRACT

Provided are a method and device for producing negative oxygen ions, and a method and device for purifying air. Said method for producing negative oxygen ions comprises: respectively introducing air and water into an air-water reactor so that the introduced air and water reach a relative movement speed of not less than 20 m/s in said air-water reactor and react within said air-water reactor so as to produce negative oxygen ions; and separating the air containing the negative oxygen ions after the reaction from the water after the reaction, and releasing the air containing the negative oxygen ions after the reaction into a required space. Said method and device can produce a large number of negative oxygen ions and purified air with a high efficiency at a low cost, without producing any harmful substances such as ozone and oxynitrides, and are long-acting and free of maintenance.

6 Claims, 4 Drawing Sheets

(51) Int. Cl.
    *B01D 49/00*     (2006.01)
    *B01D 53/72*     (2006.01)
    *C02F 1/00*     (2006.01)
    *B01D 53/00*     (2006.01)
    *B01D 53/76*     (2006.01)
    *A61L 9/14*     (2006.01)
    *F24F 3/14*     (2006.01)

(52) U.S. Cl.
    CPC ............ *B01D 53/72* (2013.01); *B01D 53/76* (2013.01); *C02F 1/00* (2013.01); *F24F 3/14* (2013.01); *F24F 3/16* (2013.01); *B01D 2251/102* (2013.01); *B01D 2257/708* (2013.01); *B01D 2257/7027* (2013.01); *B01D 2258/06* (2013.01); *F24F 2003/1682* (2013.01)

(56) References Cited

U.S. PATENT DOCUMENTS

| | | | |
|---|---|---|---|
| 2003/0035754 A1* | 2/2003 | Sias | A61L 2/14 422/29 |
| 2005/0079124 A1* | 4/2005 | Sanderson | A61L 9/145 423/477 |
| 2005/0123436 A1* | 6/2005 | Cumberland | A61L 2/10 422/5 |
| 2006/0104858 A1* | 5/2006 | Potember | A61L 9/015 422/4 |
| 2007/0217944 A1* | 9/2007 | Potember | A61L 9/015 422/4 |
| 2010/0147023 A1* | 6/2010 | Alferov | B01D 5/0048 62/606 |
| 2010/0186593 A1* | 7/2010 | Kim | B01D 53/323 96/19 |

FOREIGN PATENT DOCUMENTS

| | | |
|---|---|---|
| CN | 203264047 U | 11/2013 |
| CN | 103893810 A | 7/2014 |
| CN | 203943933 U | 11/2014 |
| EP | 0554591 | 8/1993 |
| JP | 09203540 A | 8/1997 |
| JP | H10-300139 A | 11/1998 |

OTHER PUBLICATIONS

English translation of JP 09-203540 (Year: 1997).*
European Patent Office, Extended European Search Report for corresponding EP Application No. 15780021.0, dated Nov. 30, 2017, 8 pages.
International Search Report & Written Opinion of PCT/CN2015/076595 (English Translation) dated Jul. 22, 2015.

* cited by examiner

METHOD AND DEVICE FOR PRODUCING NEGATIVE OXYGEN IONS, AND METHOD AND DEVICE FOR PURIFYING AIR

CROSS-REFERENCE TO RELATED APPLICATIONS

This application represents the national stage entry of PCT International Application PCT/CN2015/076595 filed Apr. 15, 2015 and claims priority to Chinese Patent Application 201410155480.9 filed Apr. 17, 2014. The contents of this application are hereby incorporated by reference as if set forth in their entirety herein.

TECHNICAL FIELD

The present invention relates to a method and device for producing negative oxygen ions, and a method and device for purifying air.

BACKGROUND ART

The content of negative oxygen ions is one of the important indications of air quality. The United Nations regulates that the standard of a clean air is 1000-1500 negative oxygen ions/cubic centimetres, and up to 100 thousands of negative oxygen ions/cubic centimetres are in forest districts; however, merely dozens or hundreds of negative oxygen ions/cubic centimetres are generally in cities of China, and as low as a dozen of negative oxygen ions/cubic centimetres may be in many enclosed buildings.

At present, most of the techniques for producing negative oxygen ions produce space free electrons through discharging, and the electrons are then combined with oxygen to form negative oxygen ions; but, at this time, harmful substances such as ozone and oxynitrides are also produced, which becomes an obstacle to the popularization and application of such a dry-type negative oxygen generator.

At present, there is a fullerene negative oxygen ion release agent internationally, which, however, is not extensively used yet due to a higher price.

Therefore, there is a desire for a method and device for producing negative oxygen ions, which can produce a large number of negative oxygen ions with a high efficiency at a low cost, without producing any harmful substances such as ozone.

In addition, with the aggravation of haze phenomenon, the demand for air purifiers is increasing day by day in recent years. At present, air purifiers are mostly of filtration type, i.e. air is sent to a filter by a draught fan, and passes through various filter screens having different functions and respectively achieving the effects of removing crude, medium and fine particulate matters by filtration; furthermore, there are filter screens having physical capture and chemical decomposition functions: a mineral crystal membrane, a photocatalyst decomposition membrane, an HEPA membrane, etc.

The common characteristic of the above air purifying techniques is using filter membranes to capture particulate matters in the air; when the operating time is longer or the environment is harsh, dust particles will block pores very fast, the purifying effect is decreased, and it is necessary to change consumables such as filter screens, which greatly increases the effective usage cost.

There are also some cases where high voltage electrostatic dust collection methods are used to control particulate matters in the air, which have a lower efficiency and may produce harmful substances such as ozone.

In recent years, the use of plasma or net ion flow purifiers rises abroad, which can effectively remove PM 2.5, but is difficult to popularize due to excessively high costs.

Therefore, there is a further desire for a method and device for purifying air, which can purify air with a high efficiency at a low cost, without producing any harmful substances such as ozone, and are long-acting and free of maintenance without changing consumables such as filter screens.

SUMMARY

An object of the present invention is overcoming the above-mentioned defects of the methods and devices for producing negative oxygen ions in the prior art and providing a method and device for producing negative oxygen ions, which can produce a large number of negative oxygen ions with a high efficiency at a low cost, without producing any harmful substances such as ozone.

The above object of the present invention is realized through a method for producing negative oxygen ions, comprising:

respectively introducing air and water into an air-water reactor so that the introduced air and water reach a relative movement speed of not less than 20 m/s in said air-water reactor and react within said air-water reactor so as to produce negative oxygen ions; and separating the air containing the negative oxygen ions after the reaction from the water after the reaction, and releasing the air containing the negative oxygen ions after the reaction into a required space.

According to the above-mentioned technical solution, the method for producing negative oxygen ions of the present invention can have the following beneficial technical effect: being capable of producing a large number of negative oxygen ions with a high efficiency at a low cost, without producing any harmful substances such as ozone and oxynitrides.

More preferably, the introduced water and air have a volume ratio of 5:1000 to 50:1000.

According to the above-mentioned technical solution, the method for producing negative oxygen ions of the present invention can have the following beneficial technical effect: being capable of producing a large number of negative oxygen ions with a higher efficiency.

More preferably, the introduced air and water reaching a relative movement speed of not less than 20 m/s in said air-water reactor is realized by the following way: blades at a rotational speed of 50-500 revolutions/minute strike the water in said air-water reactor to form water droplets at a speed of not less than 20 m/s so that the water droplets collide with and rub against the introduced air.

According to the above-mentioned technical solution, the method for producing negative oxygen ions of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost, without producing any harmful substances such as ozone.

More preferably, the introduced air and water reaching a relative movement speed of not less than 20 m/s in said air-water reactor is realized by the following way: an air flow at a speed of not less than 20 m/s impacts on and rubs against a water flow.

According to the above-mentioned technical solution, the method for producing negative oxygen ions of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost, without producing any harmful substances such as ozone.

More preferably, before the air flow at a speed of not less than 20 m/s impacts on and rubs against the water flow, the water flow is dispersed by a splash plate disposed in said air-water reactor.

According to the above-mentioned technical solution, the method for producing negative oxygen ions of the present invention can have the following beneficial technical effect: enabling the water flow to be sufficiently dispersed before being impacted and rubbed by the air flow at a high speed, so that a large number of negative oxygen ions can be produced with a higher efficiency.

The above object of the present invention is further realized through a device for producing negative oxygen ions, comprising:

an air-water reactor used for respectively introducing air and water so that the introduced air and water reach a relative movement speed of not less than 20 m/s in said air-water reactor and react within said air-water reactor so as to produce negative oxygen ions; and an air-water separator disposed downstream of said air-water reactor, used for separating the air containing the negative oxygen ions after the reaction from the water after the reaction and releasing the air containing the negative oxygen ions after the reaction into a required space.

According to the above-mentioned technical solution, the device for producing negative oxygen ions of the present invention can have the following beneficial technical effect: being capable of producing a large number of negative oxygen ions with a high efficiency at a low cost, without producing any harmful substances such as ozone and oxynitrides.

More preferably, the introduced water and air have a volume ratio of 5:1000 to 50:1000.

According to the above-mentioned technical solution, the device for producing negative oxygen ions of the present invention can have the following beneficial technical effect: being capable of producing a large number of negative oxygen ions with a higher efficiency.

More preferably, said air-water reactor comprises blades which are used for striking the water in said air-water reactor at a rotational speed of 50-500 revolutions/minute to form water droplets at a speed of not less than 20 m/s, so that the water droplets collide with and rub against the introduced air.

According to the above-mentioned technical solution, the device for producing negative oxygen ions of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost, without producing any harmful substances such as ozone.

More preferably, said air-water reactor comprises an air inlet portion which is used for enabling an air flow to reach a speed of not less than 20 m/s so as to impact on and rub against a water flow.

According to the above-mentioned technical solution, the device for producing negative oxygen ions of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost, without producing any harmful substances such as ozone.

More preferably, said air-water reactor further comprises a splash plate which is disposed in said air-water reactor and used for enabling the water flow to be dispersed before being impacted and rubbed by the air flow.

According to the above-mentioned technical solution, the device for producing negative oxygen ions of the present invention can have the following beneficial technical effect: enabling the water flow to be sufficiently dispersed before being impacted and rubbed by the air flow at a high speed, so that a large number of negative oxygen ions can be produced with a higher efficiency.

Another object of the present invention is overcoming the above-mentioned defects of the methods and devices for purifying air in the prior art and providing a method and device for purifying air, which can purify air with a high efficiency at a low cost, without producing any harmful substances such as ozone, and are long-acting and free of maintenance.

The above object of the present invention is realized through a method for purifying air, comprising:

respectively introducing air and water into an air-water reactor so that the introduced air and water reach a relative movement speed of not less than 20 m/s in said air-water reactor and react within said air-water reactor so as to produce negative oxygen ions and purify air; and separating the purified air containing the negative oxygen ions after the reaction from the water after the reaction, and releasing the purified air containing the negative oxygen ions after the reaction into a required space.

According to the above-mentioned technical solution, the method for purifying air of the present invention can have the following beneficial technical effect: being capable of purifying air with a high efficiency at a low cost (suitable for removing particulate matters having various concentrations and various particle sizes), without producing any harmful substances such as ozone and oxynitrides, and being long-acting and free of maintenance.

More preferably, the introduced water and air have a volume ratio of 5:1000 to 50:1000.

According to the above-mentioned technical solution, the method for purifying air of the present invention can have the following beneficial technical effect: being capable of producing a large number of negative oxygen ions and purifying air with a higher efficiency.

More preferably, the introduced air and water reaching a relative movement speed of not less than 20 m/s in said air-water reactor is realized by the following way: blades at a rotational speed of 50-500 revolutions/minute strike the water in said air-water reactor to form water droplets at a speed of not less than 20 m/s so that the water droplets collide with and rub against the introduced air.

According to the above-mentioned technical solution, the method for purifying air of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost and air is purified, without producing any harmful substances such as ozone.

More preferably, the introduced air and water reaching a relative movement speed of not less than 20 m/s in said air-water reactor is realized by the following way: an air flow at a speed of not less than 20 m/s impacts on and rubs against a water flow.

According to the above-mentioned technical solution, the method for purifying air of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost and air is purified, without producing any harmful substances such as ozone.

More preferably, before the air flow at a speed of not less than 20 m/s impacts on and rubs against the water flow, the water flow is dispersed by a splash plate disposed in said air-water reactor.

According to the above-mentioned technical solution, the method for purifying air of the present invention can have the following beneficial technical effect: enabling the water flow to be sufficiently dispersed before being impacted and rubbed by the air flow at a high speed, so that a large number of negative oxygen ions can be produced and air can be purified with a higher efficiency.

The above another object of the present invention is further realized through a device for purifying air, comprising:

an air-water reactor used for respectively introducing air and water so that the introduced air and water reach a relative movement speed of not less than 20 m/s in said air-water reactor and react within said air-water reactor so as to produce negative oxygen ions and purify air; and an air-water separator provided downstream of said air-water reactor, used for separating the purified air containing the negative oxygen ions after the reaction from the water after the reaction and releasing the purified air containing the negative oxygen ions after the reaction into a required space.

According to the above-mentioned technical solution, the device for purifying air of the present invention can have the following beneficial technical effect: being capable of purifying air with a high efficiency at a low cost (suitable for removing particulate matters having various concentrations and various particle sizes), without producing any harmful substances such as ozone and oxynitrides, and being long-acting and free of maintenance.

More preferably, the introduced water and air have a volume ratio of 5:1000 to 50:1000.

According to the above-mentioned technical solution, the device for purifying air of the present invention can have the following beneficial technical effect: being capable of purifying air with a high efficiency at a low cost, without producing any harmful substances such as ozone, and being long-acting and free of maintenance.

More preferably, said air-water reactor comprises blades which are used for striking the water in said air-water reactor at a rotational speed of 50-500 revolutions/minute to form water droplets at a speed of not less than 20 m/s, so that the water droplets collide with and rub against the introduced air.

According to the above-mentioned technical solution, the device for purifying air of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost and air is purified, without producing any harmful substances such as ozone.

More preferably, said air-water reactor comprises an air inlet portion which is used for enabling an air flow to reach a speed of not less than 20 m/s so as to impact on and rub against a water flow.

According to the above-mentioned technical solution, the device for purifying air of the present invention can have the following beneficial technical effect: the introduced air and water reaching a relative movement speed of not less than 20 m/s in said air-water reactor can be realized in a simple and efficient way, so that a large number of negative oxygen ions can be produced with a high efficiency at a low cost and air is purified, without producing any harmful substances such as ozone.

More preferably, said air-water reactor further comprises a splash plate which is disposed in said air-water reactor and used for enabling the water flow to be dispersed before being impacted and rubbed by the air flow.

According to the above-mentioned technical solution, the device for purifying air of the present invention can have the following beneficial technical effect: enabling the water flow to be sufficiently dispersed before being impacted and rubbed by the air flow at a high speed, so that a large number of negative oxygen ions can be produced and air can be purified with a higher efficiency.

LIST OF REFERENCE SIGNS IN THE DRAWINGS

101 Air-water reactor;
102 Air-water separator;
103 Induced draft fan;
104 Blade shaft;
105 Blade;
106 Electromotor;
201 Air-water reactor;
202 Air-water separator;
203 Induced draft fan;
204 Blade shaft;
205 Blade;

206 Electromotor;
207 Water pump;
208 Water sprayer;
301 Air-water reactor;
302 Air-water separator;
307 Water pump;
308 Water spray pipe;
309 Vertical plate;
401 Air-water reactor;
402 Air-water separator;
403 Induced draft fan;
408 Water spray pipe;
410 Splash plate;
411 Air inlet pipe; and
412 Inlet.

DETAILED DESCRIPTION

The present invention is further described below in conjunction with particular embodiments and drawings, and more details are set forth in the following description in order to fully understand the present invention; but it is apparent that the present invention can be implemented in many other ways different from those described herein; generalization and deduction can be made by a person skilled in the art without departing from the connotation of the present invention according to practical application, and therefore the scope of protection of the present invention should not be limited by the contents of the particular embodiments herein.

Figure 1:
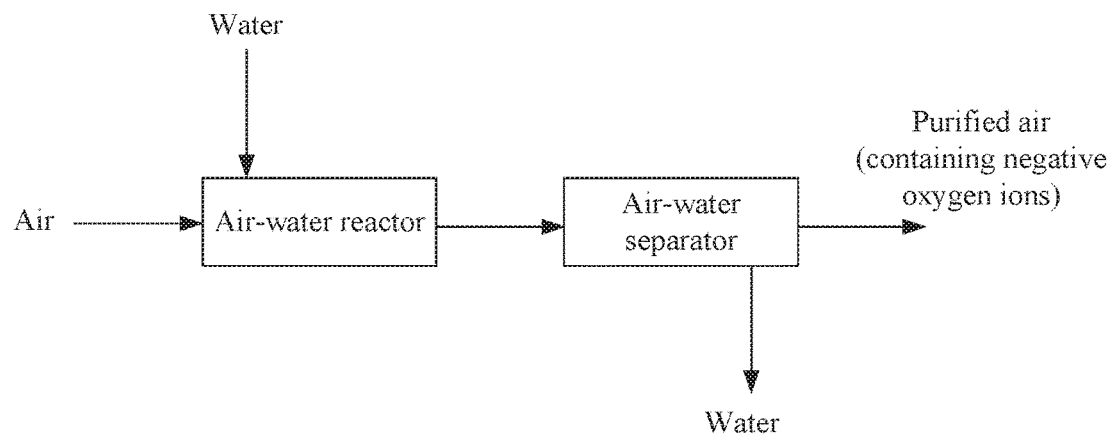
FIG. 1 is a schematic view of a method and device for producing negative oxygen ions or for purifying air according to the present invention.

FIG. 1 shows a schematic view of a method and device for producing negative oxygen ions or for purifying air according to the present invention.

As shown in FIG. 1, the method for producing negative oxygen ions or for purifying air comprises:

respectively introducing air and water into an air-water reactor so that the introduced air and water reach a relative movement speed of not less than 20 m/s in the air-water reactor and react within the air-water reactor so as to produce negative oxygen ions and purify air; and separating the purified air containing the negative oxygen ions after the reaction from the water after the reaction, and releasing the purified air containing the negative oxygen ions after the reaction into a required space.

Likewise, as shown in FIG. 1, the device for producing negative oxygen ions or for purifying air comprises:

an air-water reactor used for respectively introducing air and water so that the introduced air and water reach a relative movement speed of not less than 20 m/s in the air-water reactor and react within the air-water reactor so as to produce negative oxygen ions and purify air; and an air-water separator provided downstream of the air-water reactor, used for separating the purified air containing the negative oxygen ions after the reaction from the water after the reaction and releasing the purified air containing the negative oxygen ions after the reaction into a required space.

Since the introduced air and water reach a relative movement speed of not less than 20 m/s within the air-water reactor, the water body is cut and rubbed by the air at a high speed, and a large number of free electrons are generated in the air and combined with oxygen to form a large number of negative oxygen ions. The negative oxygen ions and water mist, for example, under the action of an induced draft fan or an air blower, enters the air-water separator, the water flows back to the bottom of the air-water reactor, and the purified air containing the negative oxygen ions is released to a required space from an air outlet of the air-water separator.

The main components of air are nitrogen, oxygen and carbon dioxide in a content of respectively 78%, 21% and 0.03%, nitrogen has no affinity to electrons, and therefore only negative ions of oxygen and carbon dioxide can be formed. Carbon dioxide molecules and oxygen molecules have substantially the same efficiency of binding to negative charges; however, the concentration of carbon dioxide in the air is only 1/700 of that of oxygen, and therefore all negative charges are substantially captured by oxygen to form negative oxygen ions.

At the same time, water (water mist and water steam) and negative oxygen ions can efficiently remove particulate matters having various particle sizes in the air so as to purify the air. Specifically, a severe relative movement of water and air in the air-water reactor has a very strong purifying effect on large particulate matters (not less than PM 2.5) in the air, and the large number of negative oxygen ions generated have a very strong purifying effect on small particulate matters (PM 2.5) in the air.

The process of removing particulate matters having different particle sizes in the air is as follows:

Large particulate matters (not less than PM 2.5) are washed, entrained and separated by the water mist in the air-water reactor, and are separated after humidifying and weight gain of the particulates.

Small particulate matters (PM 2.5) can be classified into three types, which are mainly positively charged particles and electroneutral particles as well as a very small portion of negatively charged particles.

The positively charged particles mainly include organic carbon molecules, such as formaldehyde and benzenes, and can be electrically neutralized, aggregated and separated by negative oxygen ions.

The electroneutral particles are mainly some viruses and bacteria, and the genetic materials of microorganisms can be changed by negative charges carried by negative oxygen ions, leading to the apoptosis thereof.

Negatively charged particles are mainly sulphate, hydrochloride, nitrate, chloride ions, etc., which are hydrophilic and can be removed by water mist.

More preferably, the introduced air and water reach a relative movement speed of not less than 40 m/s in the air-water reactor and react within the air-water reactor.

More preferably, the time for the air-water reaction in the air-water reactor is less than 1 s.

More preferably, the air-water separator comprises a centrifugal separator or an inclined plate inertial separator. In the case where a centrifugal separator is used as the air-water separator, more preferably, the vortex angle of the centrifugal separator is adjustable. As such, an adjustable air-water separation (dehydration) efficiency can be achieved.

According to the present invention, a range of devices for producing negative oxygen ions or for purifying air can be manufactured, which are suitable for various volumes of indoor, in-vehicle or other enclosed environments.

The present invention can provide a method and device for producing negative oxygen ions, which can produce a large number of negative oxygen ions with a high efficiency at a low cost, without producing any harmful substances such as ozone.

The present invention can further provide a method and device for purifying air, which can purify air with a high efficiency at a low cost (regardless of the original concentration and particle size of particulate matters, and also not limiting the operating time of the device), without producing any harmful substances such as ozone and oxynitrides, and are long-acting and free of maintenance.

More preferably, the present invention also has certain functions of adjusting the air humidity and air temperature.

First Embodiment

Figure 2A:
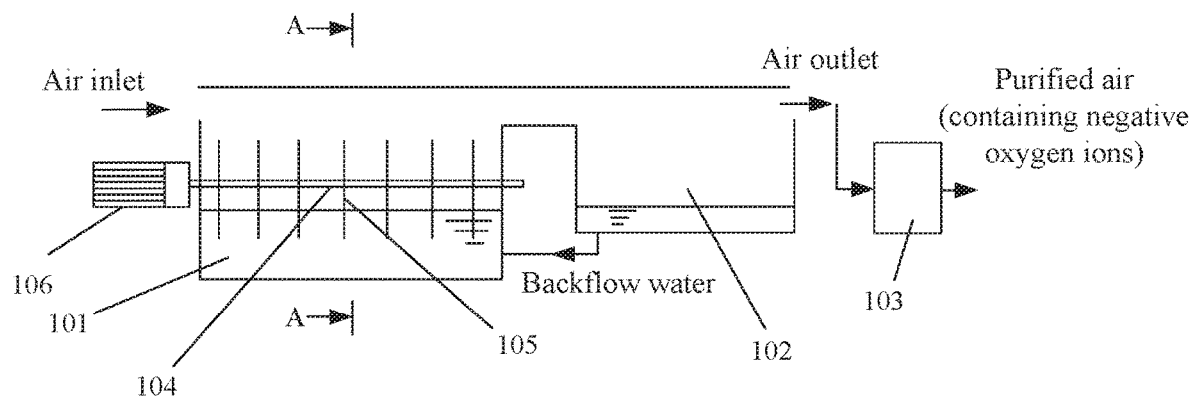
FIG. 2(a) is a schematic view of a method and device for producing negative oxygen ions or for purifying air of a first embodiment of the present invention.
Figure 2B:
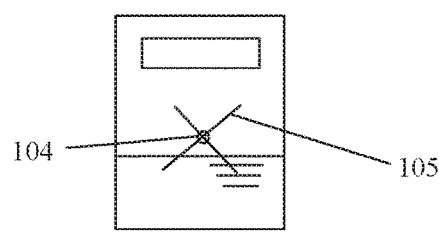
FIG. 2(b) is a cutaway view taken along a median line A-A in FIG. 2 (a).

FIG. 2(a) is a schematic view of a method and device for producing negative oxygen ions or for purifying air of a first embodiment of the present invention. FIG. 2(b) is a cutaway view taken along a median line A-A in FIG. 2(a).

The device for producing negative oxygen ions or for purifying air of the first embodiment of the present invention comprises:

an air-water reactor 101 used for respectively introducing air and water so that the introduced air and water reach a relative movement speed of not less than 20 m/s in the air-water reactor and react within the air-water reactor so as to produce negative oxygen ions and purify air; and an air-water separator 102 provided downstream of the air-water reactor 101, the air-water separator 102 being used for separating the purified air containing the negative oxygen ions after the reaction from the water after the reaction and releasing the purified air containing the negative oxygen ions after the reaction into a required space.

The air-water reactor 101 of the first embodiment of the present invention is, for example, a horizontally placed straight barrel-shaped air-water reactor. For example, the straight barrel-shaped air-water reactor has a diameter of 20 centimetres and a length of 80 centimetres.

The device for producing negative oxygen ions or for purifying air of the first embodiment of the present invention further comprises an induced draft fan 103 which is advantageously arranged downstream of the air-water separator 102 and used for more effectively releasing the purified air containing the negative oxygen ions after the reaction into a required space. Of course, a person skilled in the art will understand on the basis of the present invention that the induced draft fan can also be replaced with an air blower arranged at other position, which can also more effectively release the purified air containing the negative oxygen ions after the reaction into a required space.

The device for producing negative oxygen ions or for purifying air of the first embodiment of the present invention can further comprise a blade shaft 104 and a group or multiple groups of blades 105. The blades can strike the water in the air-water reactor 101 at a rotational speed of 50-500 revolutions/minute to form water droplets at a speed of not less than 20 m/s so that the water droplets collide with and rub against the introduced air.

The device for producing negative oxygen ions or for purifying air of the first embodiment of the present invention can further more preferably comprise an air inlet, an air outlet, a water level controller, a water inlet, a water pump, an electromotor, a speed reducer, etc.

For example, a 5*10 centimetre air inlet is provided right above and on the left side of the barrel body of the air-water reactor 101, and a 5*10 centimetre air outlet is provided right above and on the right side of the barrel body of the air-water reactor 101.

For example, the blade shaft 104 having a length of 85 centimetres runs through the barrel body and is connected with the barrel body through a sealing bushing. The end of the blade shaft 104 is connected with a speed reducer (not shown) outside the air-water reactor 101, and is driven by an electromotor 106 connected with the speed reducer. The blade shaft 104 is more preferably provided with 20 groups of four-vane blades 105. The blade 105 has a length of 6 centimetres and a width of 1 centimetre, and is designed as a rectangular plane with a thickness of 3 millimetres. Each group of blades 105 is spaced 2 centimetres apart. A water inlet is provided at the bottom of the barrel and connected with a water source, the water depth is controlled to be 6 centimetres by a water level controller, and above and on the right side of the barrel body, the air-water separator 102 is connected with the air outlet. The air-water separator 102 is more preferably a multi-tube cyclone demister. A water outlet for flowing the separated water back to the air-water reactor 101 is provided at the bottom of the air-water separator 102.

During operation, for example, the electromotor 106 drives the blades 105 to rotate at a speed of 120 revolutions per second so as to strike the liquid surface at a high speed to produce a great number of water droplets, the water droplets can be accelerated to a maximum speed of 43 metres per second, the accelerated water droplets cut and rub against the air at a high speed, leading the water to lose electrons, the lost electrons become space free electrons, and the space free electrons are combined with oxygen to form a large number of negative oxygen ions. The negative oxygen ions and water mist, under the action of the induced draft fan 103, enters the air-water separator 102, the separated water flows back to the bottom of the air-water reactor 101, and the air containing the negative oxygen ions is discharged from the air outlet of the air-water separator 102.

After passing through the air-water reactor 101, the water and air enter the air-water separator 102. Under the action of centrifugal force, various particulate matters are ultimately separated together with the water body, and flow into a water tank and precipitated, thereby completing the removal. The air only carries negative oxygen ions back to the room, and the negative oxygen ions diffuse within the room to continue the removal of indoor PM 2.5.

More preferably, the inner wall of the air-water separator is smooth and has no concave-convex structure. As such, the water droplets are ensured to always maintain a speed of not less than 20 m/s.

More preferably, the outer surfaces of the blades are rough. As such, it is ensured that water droplets can be effectively picked up when the blades strike the water surface.

More preferably, the cross section of the blade is in a roughly rectangular shape. As such, it is further ensured that water droplets can be effectively picked up when the blades strike the water surface, and furthermore, the water droplets have a speed of not less than 20 m/s.

The device for producing negative oxygen ions or for purifying air which is suitable for various enclosed spaces can achieve the objects only by adjusting the equipment power and size.

Second Embodiment

Figure 3:
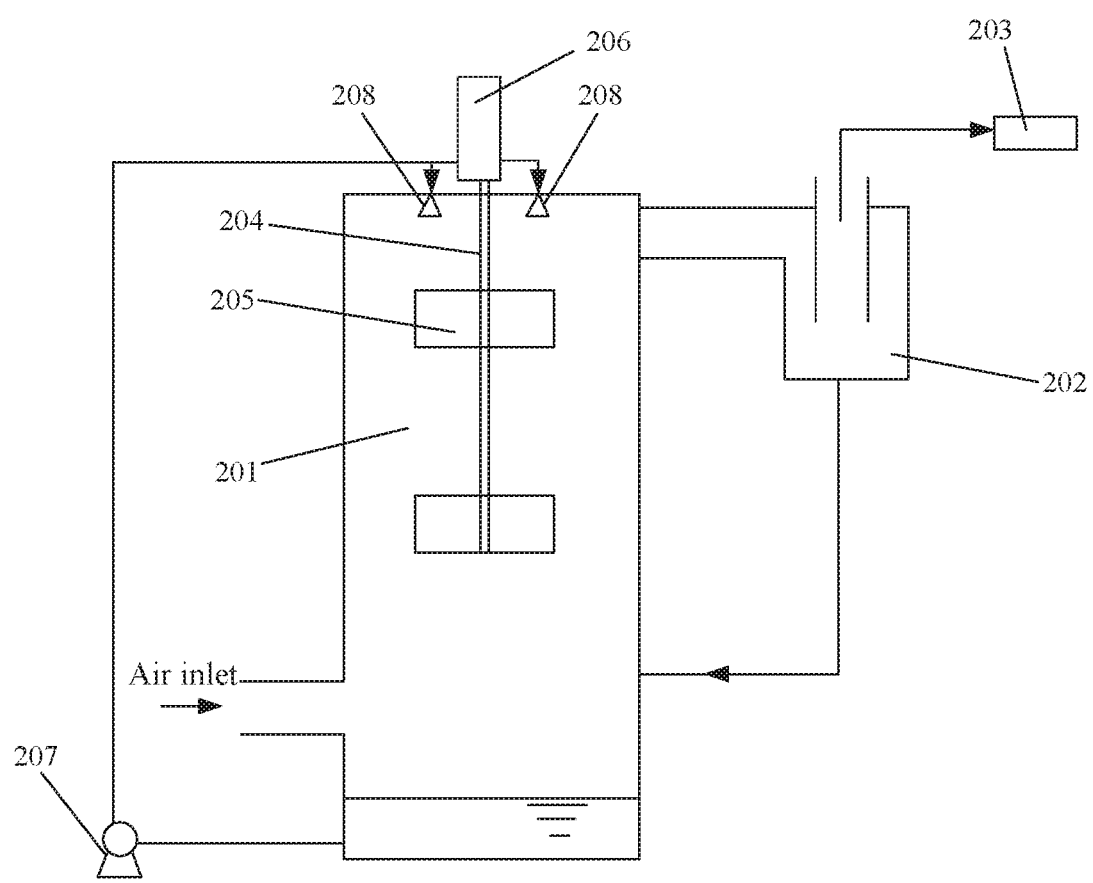
FIG. 3 is a schematic view of a method and device for producing negative oxygen ions or for purifying air of a second embodiment of the present invention.

FIG. 3 is a schematic view of a method and device for producing negative oxygen ions or for purifying air of a second embodiment of the present invention.

The device for producing negative oxygen ions or for purifying air of the second embodiment of the present invention comprises:

an air-water reactor 201 used for respectively introducing air and water so that the introduced air and water reach a relative movement speed of not less than 20 m/s in the air-water reactor and react within the air-water reactor so as to produce negative oxygen ions and purify air; and an air-water separator 202 provided downstream of the air-water reactor 201, the air-water separator 202 being used for separating the purified air containing the negative oxygen ions after the reaction from the water after the reaction and releasing the purified air containing the negative oxygen ions after the reaction into a required space.

The air-water reactor 201 of the second embodiment of the present invention is, for example, a vertically placed straight barrel-shaped air-water reactor. For example, the straight barrel-shaped air-water reactor has a diameter of 20 centimetres and a height of 80 centimetres.

The device for producing negative oxygen ions or for purifying air of the second embodiment of the present invention further comprises an induced draft fan 203 which is advantageously arranged downstream of the air-water separator 202 and used for more effectively releasing the purified air containing the negative oxygen ions after the reaction into a required space. Of course, a person skilled in the art will understand on the basis of the present invention that the induced draft fan can also be replaced with an air blower arranged at other position, which can also more effectively release the purified air containing the negative oxygen ions after the reaction into a required space.

The device for producing negative oxygen ions or for purifying air of the second embodiment of the present invention can further comprise a blade shaft 204 and a group or multiple groups of blades 205. The blades can strike the water sprinkled from water sprayers 208 in the air-water reactor 201 at a rotational speed of 50-500 revolutions/minute to form water droplets at a speed of not less than 20 m/s so that the water droplets collide with and rub against the introduced air.

The device for producing negative oxygen ions or for purifying air of the second embodiment of the present invention can further more preferably comprise an air inlet, an air outlet, a water inlet, a water pump 207, an electromotor 206, a speed reducer, etc.

For example, a 5*10 centimetre air outlet is provided on the side face at the top of the air-water reactor 201, and two water sprayers 208 having a diameter of 9 centimetres are arranged 10 centimetres below the air outlet. The blade shaft 204 has a height of 40 centimetres, 4 groups of blades on the blade shaft all have a height of 2 centimetres and a length of 9.6 centimetres, and the 4 groups of blades are arranged, in an angularly staggered manner, within an interval of 5-20 centimetres below the water sprayers 208. A 5*10 centimetre air inlet is opened on the reactor wall at a distance of 20 centimetres from the bottom of the air-water reactor 201. An open-type water tank is provided in the lower portion of the air-water reactor 201, and has a liquid level height of 10 centimetres.

During operation, for example, the water pump 207 sprays the water in the water tank at the bottom of the air-water reactor 201 at a flow rate of 0.2 litres per second from the water sprayers 208. The 4 groups of blades, under the drive of the electromotor, simultaneously operate at a rotational speed of 120 revolutions per second and strike the sprayed water body at a high speed, the water droplets can be accelerated to a maximum speed of 72 metres per second, the accelerated water droplets cut and rub against the air at a high speed, leading the water to lose electrons, the lost electrons become space free electrons, and the space free electrons are combined with oxygen to form a large number of negative oxygen ions. The air carrying the water mist and negative oxygen ions enters the air-water separator 202 from the air outlet, and the water is separated and flows back to the water tank. The air containing the negative oxygen ions is discharged from the air outlet of the air-water separator 202.

The device for producing negative oxygen ions or for purifying air which is suitable for various enclosed spaces can achieve the objects only by adjusting the equipment power and size.

Third Embodiment

Figure 4:
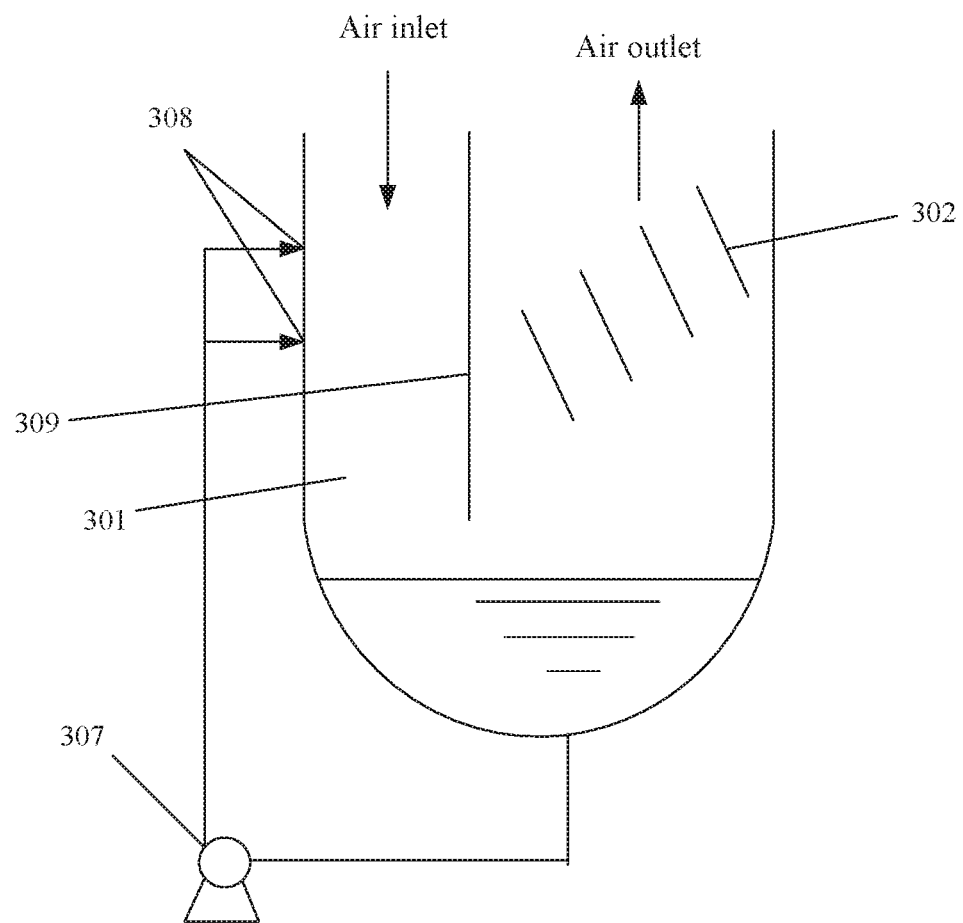
FIG. 4 is a schematic view of a method and device for producing negative oxygen ions or for purifying air of a third embodiment of the present invention.

FIG. 4 is a schematic view of a method and device for producing negative oxygen ions or for purifying air of a third embodiment of the present invention.

The device for producing negative oxygen ions or for purifying air of the third embodiment of the present invention comprises:

an air-water reactor 301 used for respectively introducing air and water so that the introduced air and water reach a relative movement speed of not less than 20 m/s in the air-water reactor and react within the air-water reactor so as to produce negative oxygen ions and purify air; and an air-water separator 302 provided downstream of the air-water reactor 301, the air-water separator 302 being used for separating the purified air containing the negative oxygen ions after the reaction from the water after the reaction and releasing the purified air containing the negative oxygen ions after the reaction into a required space.

The air-water reactor 301 of the third embodiment of the present invention is, for example, a long cube-shaped air-water reactor. For example, the air-water reactor 301 has a length of 30 centimetres, a width of 20 centimetres, and a height of 60 centimetres.

The device for producing negative oxygen ions or for purifying air of the third embodiment of the present invention can further more preferably comprises an air inlet, an air outlet, water spray pipes 308, a water pump 307, etc.

For example, the upper surface of the air-water reactor 301 is open, and a vertical plate 309 is provided in the upper portion to divide the tank body into two parts respectively having a length of 10 centimetres and 20 centimetres, the narrow side being the air inlet, and the wide side being the air outlet. The vertical plate 309 is aligned with the upper surface of the tank body and at a distance of 20 centimetres from the bottom of the tank body. A water tank having a water depth of 15 centimetres and more preferably provided with a water level controller is provided at the bottom of the tank body and connected with a water source. Two water spray pipes 308 having a sectional area of 1 square millimetre are provided on the outer surface on the narrow side of the air-water reactor 301, and are at a distance of 15 centimetres from the top of the tank body. The water spray pipes 308 are connected with the water tank at the bottom of the tank body via the water pump 307. The water pump 307 has a pressure of 0.4 MPa and a flow rate of 1 litre per second. An air-water separator 302 is provided in the upper portion on the wide side. The air-water separator 302 is, for example, a group of inclined plate inertial dehydraters having an inclined angle of 55 degrees. The air outlet in the upper portion of the tank body is connected with an induced draft fan.

During operation, for example, the water pump 307 sprays the water flow at a pressure of 0.4 MPa through the water spray pipes 308, the water flow strikes onto the vertical plate 309 and cuts and rubs against the air at a high speed, leading the water to lose electrons, the lost electrons become space free electrons, and the space free electrons are combined with oxygen to form a large number of negative oxygen ions. The negative oxygen ions and water mist, under the action of the induced draft fan, enters the air-water separator 302 (inclined plate inertial dehydrater) on the right side, the separated water flows back to the bottom of the air-water reactor 301, and the air containing the negative oxygen ions is discharged from an air outlet of the induced draft fan.

The device for producing negative oxygen ions or for purifying air which is suitable for various enclosed spaces can achieve the objects only by adjusting the equipment power and size.

Fourth Embodiment

Figure 5A:
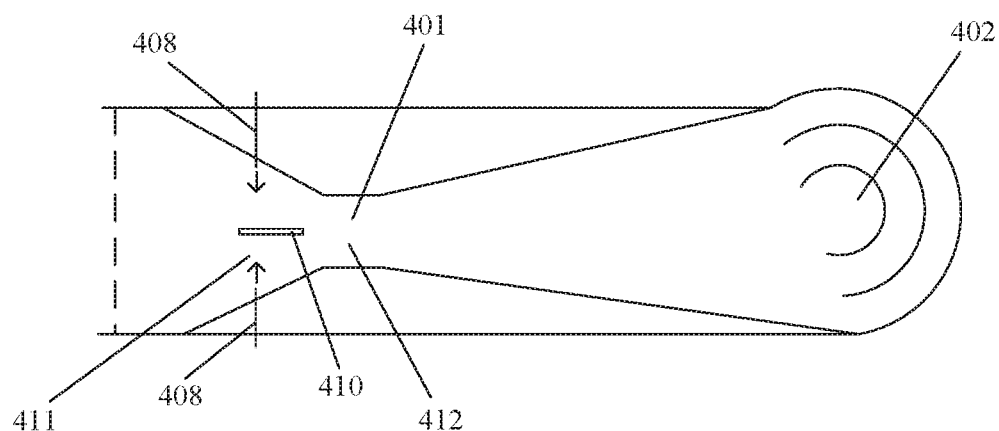
FIG. 5(a) is a schematic top view of a method and device for producing negative oxygen ions or for purifying air of a fourth embodiment of the present invention.
Figure 5B:
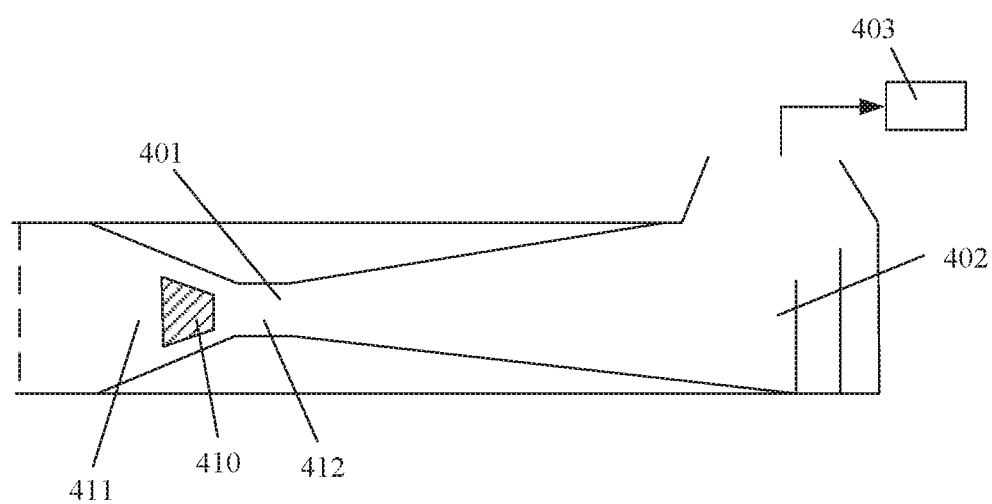
FIG. 5(b) is a schematic side view of a method and device for producing negative oxygen ions or for purifying air of a fourth embodiment of the present invention.

FIG. 5(a) is a schematic top view of the method and device for producing negative oxygen ions or for purifying air of a fourth embodiment of the present invention, and FIG. 5(b) is a schematic side view of the method and device for producing negative oxygen ions or for purifying air of a fourth embodiment of the present invention.

The device for producing negative oxygen ions or for purifying air of the fourth embodiment of the present invention comprises:

an air-water reactor 401 used for respectively introducing air and water so that the introduced air and water reach a relative movement speed of not less than 20 m/s in the air-water reactor and react within the air-water reactor so as to produce negative oxygen ions and purify air; and an air-water separator 402 provided downstream of the air-water reactor 401, the air-water separator 402 being used for separating the purified air containing the negative oxygen ions after the reaction from the water after the reaction and releasing the purified air containing the negative oxygen ions after the reaction into a required space.

Here introduces a method and device for producing negative oxygen ions or for purifying air which are suitable for an area of 40 m$^2$ and a space of 120 m$^3$ of the fourth embodiment of the present invention. According to one full circulation of air in a room of 20 minutes, then the flow rate of the draught fan is 120 m$^3$/20 min=360 m$^3$/h=0.1 m$^3$/s, and the air pressure is 2500 Pa.

For example, air is sucked into an air inlet pipe 411 (also referred to as "an air inlet portion") from an air inlet having a sectional area of 200 cm$^2$ by the draught fan, the air having a speed of 5 m/s, and the sectional area of the air inlet pipe is narrowed down at the end of the pipe, so that the air speed is accelerated to 40 m/s (of course, the air speed of 40 m/s herein is only exemplary, and with the principle of the present invention, it is allowable as long as an air flow at a speed of not less than 20 m/s is used) and enters an inlet 412 of the air-water reactor 401, a water pump and water spray pipes 408 are used in front of the inlet 412 to spray water into the air-water reactor 401, the water rushes to a splash plate 410 in front of the inlet 412 and is scattered, and is then repeatedly cut and rubbed by the air at a high speed, leading the water to lose electrons, the lost electrons become space free electrons, and the space free electrons are combined with oxygen to form a large number of negative oxygen ions. At the same time, a great amount of water mist and water steam is formed in the air-water reactor 401.

The negative oxygen ions and water mist, for example, under the action of an induced draft fan 403, enters the air-water separator 402 on the right side. Under the action of centrifugal force, various particulate matters are ultimately separated together with the water body, and flow into a water tank and precipitated, thereby completing the removal. The air only carries negative oxygen ions and part of water steam back to the room, and the negative oxygen ions diffuse within the room to continue the removal of indoor PM 2.5.

More preferably, the introduced water and air have a volume ratio of 5:1000 to 50:1000.

More preferably, the air flow at a speed of not less than 20 m/s is generated by varying the diameter of the air inlet passage.

The method and device have a one-time removal rate of particulate matters having various particle sizes in the air flowing through the air-water reactor, which can reach not less than 95%.

The device for producing negative oxygen ions or for purifying air which is suitable for various enclosed spaces can achieve the objects only by adjusting the equipment power and size.

Although the four embodiments provided above describe methods and devices for producing negative oxygen ions or for purifying air with a particular construction, a person skilled in the art will understand on the basis of the present invention that the scope of protection of the present invention is not limited to the above listed methods and devices for producing negative oxygen ions or for purifying air with a particular construction, and methods and devices for producing negative oxygen ions or for purifying air with other constructions can also be used. According to the principle of the present invention, it is allowable as long as a method for producing negative oxygen ions or for purifying air comprises the following steps: respectively introducing air and water into an air-water reactor so that the introduced air and water reach a relative movement speed of not less than 20 m/s in the air-water reactor and react within the air-water reactor so as to produce negative oxygen ions and purify air; and separating the purified air containing the negative oxygen ions after the reaction from the water after the reaction, and releasing the purified air containing the negative oxygen ions after the reaction into a required space. Or, according to the principle of the present invention, it is allowable as long as a device for producing negative oxygen ions or for purifying air comprises the following air-water reactor and air-water separator: the air-water reactor is used for respectively introducing air and water so that the introduced air and water reach a relative movement speed of not less than 20 m/s in the air-water reactor and react within the air-water reactor so as to produce negative oxygen ions and purify air; and the air-water separator is provided downstream of the air-water reactor, the air-water separator being used for separating the purified air containing the negative oxygen ions after the reaction from the water after the reaction and releasing the purified air containing the negative oxygen ions after the reaction into a required space.

In addition to the functions of producing negative oxygen ions and purifying air, more preferably, the present invention may further have a function of adjusting the temperature and humidity, that is, the present invention may be an air conditioning device operating on a new principle.

More preferably, the method for producing negative oxygen ions or for purifying air further comprises adjusting the temperature of the water before introducing the water into said air-water reactor so as to adjust the temperature of the released air.

More preferably, the device for producing negative oxygen ions or for purifying air further comprises a water temperature regulator which is used for adjusting the temperature of the water before introducing the water into said air-water reactor so as to adjust the temperature of the released air.

The principle of adjusting the air temperature of the present invention is as follows: the temperature of the released air can be adjusted as long as the temperature of the water introduced into the air-water reactor is adjusted, because in the air-water reactor, the water body is fully mixed with the air, and the two directly exchange heat with each other so as to rapidly change the temperature of the released air.

The present invention can also adjust the air humidity, and the principle thereof is as follows: in dry seasons, since the output air flow in the present invention contains water vapour, indoor humidification can be effected; and in high-humidity seasons, after sucking a high-humidity indoor air, the air-water reactor of the present invention coagulates and liquefies part of the water vapour and separates same from air in a dehydrater, and the water no longer enters the room, leading to a reduction in indoor humidity.

More preferably, the present invention is used as an air conditioner of a new principle, which has three significances:

I. Traditional air-conditioners all heat or cool air indirectly, while the present invention performs heat exchange by bringing water into direct contact with air, so that the efficiency is greatly improved.

II. The air outputted from traditional air-conditioners is dry air so that human body may feel uncomfortable, while the present invention can maintain the indoor environment at a liveable relative humidity environment.

III. Traditional air-conditioners can neither remove PM 2.5 and harmful gases such as formaldehyde from the air, nor produce negative oxygen ions to improve the air quality, while the present invention can simultaneously achieve the above functions.

The present invention has been exemplarily described above in conjunction with the accompanying drawings, and obviously, the specific implementation of the present invention is not limited to the above embodiments. Various modifications or variations can be made by a person skilled in the art on the premise of not departing from the technical concept of the present invention, and such modifications or variations of course fall within the protection scope of the present invention.

The invention claimed is:

1. A device for producing negative oxygen ions, comprising:
an air-water reactor used for introducing air and water, wherein the air-water reactor with a first sectional area comprises an air inlet pipe with a second sectional area, the second sectional area of the air inlet pipe decreases in the direction of flow and the first sectional area of the air-water reactor increases in the direction of flow, so that the introduced air and water reach a relative movement speed of not less than 20 m/s in said air-water reactor and react within said air-water reactor so as to produce negative oxygen ions; and
an air-water separator disposed downstream of said air-water reactor, used for separating air containing the negative oxygen ions from the water after the reaction and releasing the air containing the negative oxygen ions after the reaction into a required space,
wherein said air-water reactor further comprises a splash plate which is disposed in said air-water reactor and used for enabling the water flow to be dispersed before being impacted and rubbed by the air flow.

2. A device for producing negative oxygen ions, comprising:
an air-water reactor used for introducing air and water, wherein the air-water reactor with a first sectional area comprises an air inlet pipe with a second sectional area, the second sectional area of the air inlet pipe decreases in the direction of flow and the first sectional area of the air-water reactor increases in the direction of flow, so that the introduced air and water reach a relative movement speed of not less than 20 m/s in said air-water reactor and react within said air-water reactor so as to produce negative oxygen ions;
an air-water separator disposed downstream of said air-water reactor, used for separating air containing the negative oxygen ions from the water after the reaction and releasing the air containing the negative oxygen ions after the reaction into a required space; and
a water temperature regulator which is used for adjusting the temperature of water before introducing the water into said air-water reactor so as to adjust the temperature of the released air.

3. A method for producing negative oxygen ions, comprising:
introducing air and water into an air-water reactor with a first sectional area, wherein the air-water reactor comprises an air inlet pipe with a second sectional area, the second sectional area of the air inlet pipe decreases in the direction of flow and the first sectional area of the air-water reactor increases in the direction of flow, so that the introduced air and water reach a relative movement speed of not less than 20 m/s in said air-water reactor and react within said air-water reactor so as to produce negative oxygen ions; and
separating air containing the negative oxygen ions from the water after the reaction, and releasing the air containing the negative oxygen ions after the reaction into a required space.

4. The method for producing negative oxygen ions of claim 3, wherein the introduced water and air have a volume ratio of 5:1000 to 50:1000.

5. The method for producing negative oxygen ions of claim 3, wherein before the air flow at a speed of not less than 20 m/s impacts on and rubs against the water flow, the water flow is dispersed by a splash plate disposed in said air-water reactor.

6. The method for producing negative oxygen ions of claim 3, further comprising: adjusting the temperature of water before introducing the water into said air-water reactor so as to adjust the temperature of the released air.

* * * * *